US009622792B2

(12) United States Patent
Pool et al.

(10) Patent No.: US 9,622,792 B2
(45) Date of Patent: Apr. 18, 2017

(54) INTERSPINOUS PROCESS DEVICE AND METHOD

(75) Inventors: Scott Pool, Laguna Hills, CA (US); Arvin Chang, Yorba Linda, CA (US); Peter P. Tran, Irvine, CA (US); Blair Walker, Mission Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 343 days.

(21) Appl. No.: 12/761,141

(22) Filed: Apr. 15, 2010

(65) Prior Publication Data

US 2010/0280551 A1    Nov. 4, 2010

Related U.S. Application Data

(60) Provisional application No. 61/173,902, filed on Apr. 29, 2009.

(51) Int. Cl.
*A61B 17/70* (2006.01)

(52) U.S. Cl.
CPC .................. *A61B 17/7065* (2013.01)

(58) Field of Classification Search
CPC ............ A61B 17/7065; A61B 17/7016; A61B 17/7067; A61B 2017/0256;
(Continued)

(56) References Cited

U.S. PATENT DOCUMENTS 5,290,312 A * 3/1994 Kojimoto ................. A61F 2/44
                                                       606/247
5,676,665 A * 10/1997 Bryan ........................... 606/252
(Continued)

FOREIGN PATENT DOCUMENTS

| WO | WO2006090380 A2 | 8/2006 |
|---|---|---|
| WO | WO2007015239 A2 | 2/2007 |
| WO | WO2007118179 A2 | 10/2007 |

OTHER PUBLICATIONS

Micromotion "Micro Drive Engineering-General catalogue" pp. 14-24; Jun. 2009.*

(Continued)

*Primary Examiner* — Jan Christopher Merene
*Assistant Examiner* — Atiya Mahmud
(74) *Attorney, Agent, or Firm* — Jeremy A. Smith; Bradley Arant Boult Cummings LLP

(57) ABSTRACT

An interspinous process device is configured for placement between adjacent spinous processes on a subject's spine. The device includes a housing configured for mounting to a first spinal process, the housing having a lead screw fixedly secured at one end thereof. A magnetic assembly is at least partially disposed within the housing and configured for mounting to a second spinal process. The magnetic assembly includes a hollow magnet configured for rotation within the magnetic assembly, the hollow magnet comprising a threaded insert configured to engage with the lead screw. An externally applied magnetic field rotates the hollow magnet in a first direction or a second, opposite direction. Rotation of the hollow magnet in the first direction causes telescopic movement of the magnetic assembly out of the housing (i.e., elongation) and rotation in the second direction causes telescopic movement of the magnetic assembly into the housing (i.e., shortening).

36 Claims, 11 Drawing Sheets

(58) Field of Classification Search
CPC ... A61B 2017/0275; A61F 2002/30079; A61F 2002/30405
USPC .......... 606/246, 248, 249; 623/18.11, 17.11, 623/17.15
See application file for complete search history.

(56) References Cited

U.S. PATENT DOCUMENTS

| | | | |
|---|---|---|---|
| 5,704,939 | A | 1/1998 | Justin |
| 6,022,349 | A * | 2/2000 | McLeod et al. ............... 606/58 |
| 6,126,664 | A | 10/2000 | Troxell et al. |
| 6,375,682 | B1 | 4/2002 | Fleischmann et al. |
| 6,416,516 | B1 | 7/2002 | Stauch et al. |
| 6,417,750 | B1 | 7/2002 | Sohn |
| 6,706,042 | B2 | 3/2004 | Taylor |
| 6,849,076 | B2 | 2/2005 | Blunn et al. |
| 7,063,706 | B2 | 6/2006 | Wittenstein |
| 7,357,635 | B2 | 4/2008 | Belfor et al. |
| 7,458,981 | B2 * | 12/2008 | Fielding et al. ............. 606/279 |
| 7,531,002 | B2 | 5/2009 | Sutton et al. |
| 7,601,156 | B2 | 10/2009 | Robinson |
| 7,608,104 | B2 * | 10/2009 | Yuan et al. ................ 623/17.11 |
| 7,611,526 | B2 | 11/2009 | Carl et al. |
| 7,666,184 | B2 | 2/2010 | Stauch |
| 7,776,091 | B2 * | 8/2010 | Mastrorio et al. ......... 623/17.15 |
| 7,794,476 | B2 | 9/2010 | Wisnewski |
| 7,811,328 | B2 | 10/2010 | Molz, IV et al. |
| 7,862,502 | B2 | 1/2011 | Pool et al. |
| 7,887,566 | B2 | 2/2011 | Hynes |
| 7,955,357 | B2 | 6/2011 | Kiester |
| 7,981,025 | B2 | 7/2011 | Pool et al. |
| 8,043,299 | B2 | 10/2011 | Conway |
| 8,057,472 | B2 | 11/2011 | Walker et al. |
| 8,105,363 | B2 | 1/2012 | Fielding et al. |
| 8,147,517 | B2 | 4/2012 | Trieu et al. |
| 8,147,549 | B2 | 4/2012 | Metcalf et al. |
| 8,177,789 | B2 | 5/2012 | Magill et al. |
| 8,211,179 | B2 | 7/2012 | Molz, IV et al. |
| 8,216,275 | B2 | 7/2012 | Fielding et al. |
| 8,221,420 | B2 | 7/2012 | Keller |
| 8,241,331 | B2 | 8/2012 | Arnin |
| 8,246,533 | B2 | 8/2012 | Chang et al. |
| 8,252,063 | B2 | 8/2012 | Stauch |
| 8,298,240 | B2 | 10/2012 | Giger et al. |
| 8,419,801 | B2 | 4/2013 | DiSilvestro et al. |
| 8,439,915 | B2 | 5/2013 | Harrison et al. |
| 8,469,908 | B2 | 6/2013 | Asfora |
| 8,486,110 | B2 | 7/2013 | Fielding et al. |
| 8,529,606 | B2 | 9/2013 | Alamin et al. |
| 8,562,653 | B2 | 10/2013 | Alamin et al. |
| 8,632,544 | B2 | 1/2014 | Haaja et al. |
| 8,894,663 | B2 | 11/2014 | Giger et al. |
| 8,968,406 | B2 | 3/2015 | Arnin |
| 2003/0144669 | A1 | 7/2003 | Robinson |
| 2004/0023623 | A1 | 2/2004 | Stauch et al. |
| 2004/0030395 | A1 * | 2/2004 | Blunn et al. ............... 623/18.12 |
| 2005/0090823 | A1 | 4/2005 | Bartim |
| 2005/0096744 | A1 * | 5/2005 | Trieu .................... A61F 2/4611 623/17.11 |
| 2005/0159754 | A1 | 7/2005 | Odrich |
| 2005/0244499 | A1 | 11/2005 | Diaz et al. |
| 2006/0004459 | A1 * | 1/2006 | Hazebrouck et al. ...... 623/18.12 |
| 2006/0079897 | A1 * | 4/2006 | Harrison et al. ............... 606/61 |
| 2006/0235424 | A1 | 10/2006 | Vitale et al. |
| 2006/0241601 | A1 * | 10/2006 | Trautwein et al. ............. 606/61 |
| 2006/0241614 | A1 * | 10/2006 | Bruneau et al. ................ 606/69 |
| 2006/0293662 | A1 * | 12/2006 | Boyer et al. ................... 606/61 |
| 2006/0293683 | A1 | 12/2006 | Stauch |
| 2007/0010814 | A1 | 1/2007 | Stauch |
| 2007/0093823 | A1 * | 4/2007 | Booth et al. ................... 606/61 |
| 2007/0173826 | A1 * | 7/2007 | Canaveral et al. ............ 606/61 |
| 2007/0173837 | A1 | 7/2007 | Chan et al. |
| 2007/0213751 | A1 * | 9/2007 | Scirica et al. ................ 606/157 |
| 2007/0255413 | A1 * | 11/2007 | Edie et al. .................. 623/17.16 |
| 2007/0264605 | A1 | 11/2007 | Belfor et al. |
| 2007/0270803 | A1 * | 11/2007 | Giger et al. .................... 606/60 |
| 2007/0276368 | A1 | 11/2007 | Trieu et al. |
| 2007/0276369 | A1 * | 11/2007 | Allard et al. ................... 606/61 |
| 2007/0276378 | A1 * | 11/2007 | Harrison et al. ............... 606/61 |
| 2008/0027435 | A1 | 1/2008 | Zucherman et al. |
| 2008/0033436 | A1 * | 2/2008 | Song et al. ..................... 606/61 |
| 2008/0039943 | A1 | 2/2008 | Le Couedic |
| 2008/0051800 | A1 | 2/2008 | Diaz et al. |
| 2008/0097188 | A1 | 4/2008 | Pool et al. |
| 2008/0097496 | A1 * | 4/2008 | Chang et al. ................ 606/157 |
| 2008/0161933 | A1 | 7/2008 | Grotz et al. |
| 2008/0167685 | A1 | 7/2008 | Allard et al. |
| 2008/0172072 | A1 | 7/2008 | Pool et al. |
| 2008/0228186 | A1 | 9/2008 | Gall et al. |
| 2008/0255615 | A1 | 10/2008 | Vittur et al. |
| 2009/0030462 | A1 | 1/2009 | Buttermann |
| 2009/0076579 | A1 | 3/2009 | Dahlgren et al. |
| 2009/0082820 | A1 * | 3/2009 | Fielding et al. ............. 606/326 |
| 2009/0093890 | A1 | 4/2009 | Gelbart |
| 2009/0112207 | A1 * | 4/2009 | Walker et al. .................. 606/57 |
| 2009/0112262 | A1 | 4/2009 | Pool et al. |
| 2009/0125062 | A1 | 5/2009 | Arnin |
| 2009/0171356 | A1 | 7/2009 | Klett |
| 2009/0192514 | A1 | 7/2009 | Feinberg et al. |
| 2009/0248079 | A1 * | 10/2009 | Kwak et al. .................. 606/249 |
| 2009/0248148 | A1 * | 10/2009 | Shaolian et al. ............. 623/2.37 |
| 2009/0264929 | A1 * | 10/2009 | Alamin et al. ................ 606/248 |
| 2010/0049204 | A1 * | 2/2010 | Soubeiran ...................... 606/90 |
| 2010/0100185 | A1 | 4/2010 | Trieu et al. |
| 2010/0114103 | A1 * | 5/2010 | Harrison et al. ................ 606/90 |
| 2010/0137911 | A1 * | 6/2010 | Dant ............................ 606/252 |
| 2010/0249847 | A1 | 9/2010 | Jung et al. |
| 2011/0118848 | A1 * | 5/2011 | Faccioli .................... A61F 2/36 623/22.11 |
| 2011/0257655 | A1 | 10/2011 | Copf et al. |
| 2012/0203282 | A1 | 8/2012 | Sachs et al. |
| 2015/0105824 | A1 | 4/2015 | Moskowitz et al. |

OTHER PUBLICATIONS

Gebhart, M., Neel, M., Soubeiran, A., Dubousset, J., "Early clinical experience with a custom made growing endoprosthesis in children with malignant bone tumors of the lower extremity actioned by an external permanent magnet: the Phenix M system", International Society of Limb Salvage 14th International Symposium on Limb Salvage, Sep. 13, 2007, Hamburg, Germany.

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.

Soubeiran, A., Gebhart, M., Miladi, L., Griffet, J., Neel, M., Dubousset, J., "The Phenix M system, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany.

Verkerke, G., Koops, H., Veth, R., Oldhoff, J., Nielsen, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.

Verkerke, G., Koops, H., Veth, R., van den Kroonenberg, H., Grootenboer, H., Nielsen, H., Oldhoff, J., Postma, A., "An Extendable Modular Endoprosthetic System for Bone Tumour Management in the Leg", Journal of Biomedical Engineering, 1990, vol. 12, No. 2, pp. 91-96, Butterfield Scientific Limited, Guilford, England.

* cited by examiner

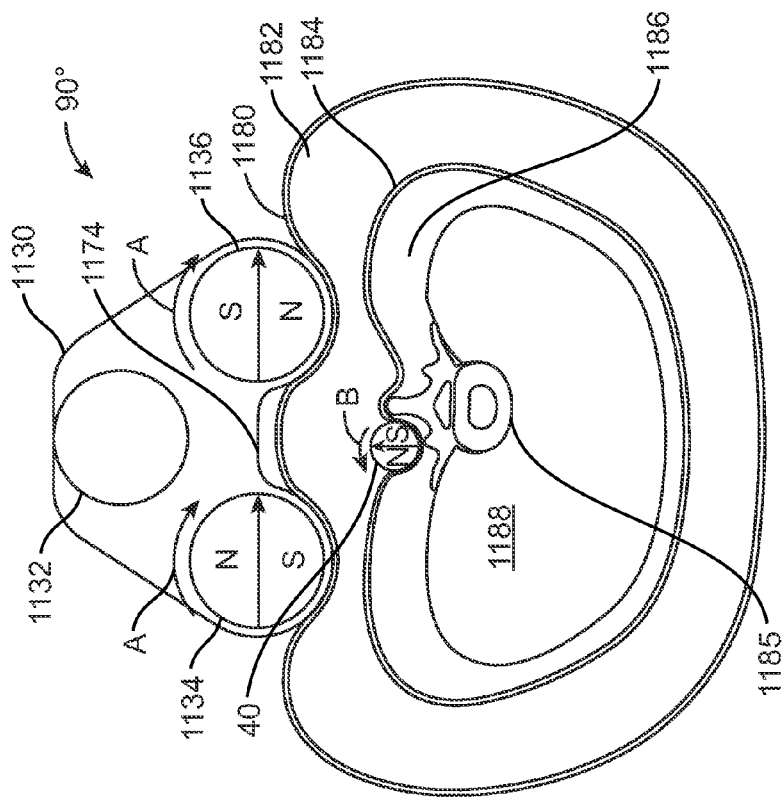
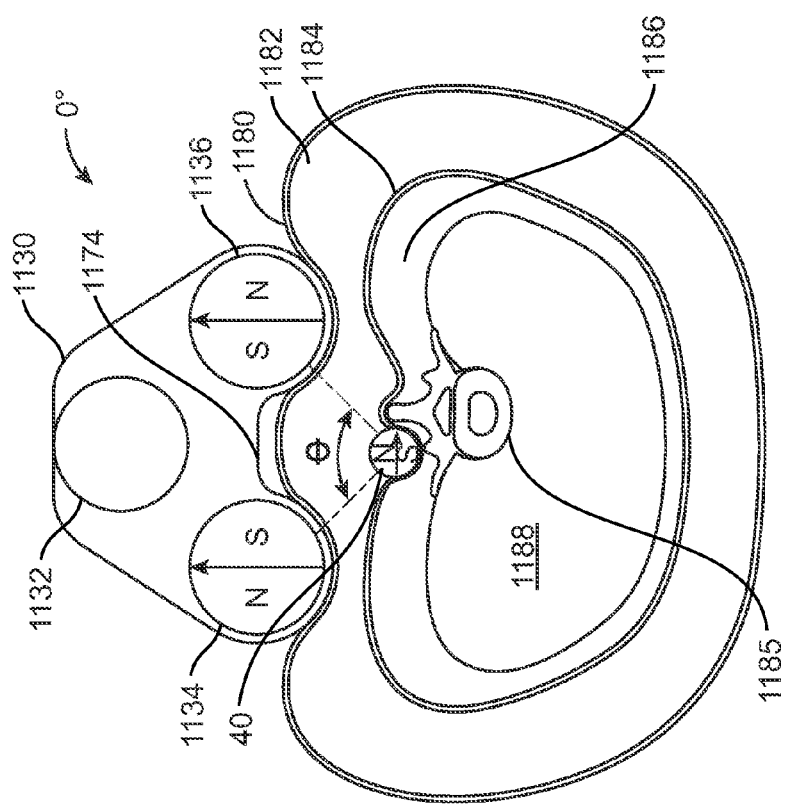

INTERSPINOUS PROCESS DEVICE AND METHOD

REFERENCE TO RELATED APPLICATIONS

This Application claims priority to U.S. Provisional Patent Application No. 61/173,902 filed on Apr. 29, 2009. U.S. Provisional Patent Application No. 61/173,902 is incorporated by reference as if set forth fully herein.

FIELD OF THE INVENTION

The field of the invention generally relates to medical devices for treating disorders of the skeletal system and in particular the spinal system.

BACKGROUND OF THE INVENTION

As individuals age, their spinal discs tend to degenerate over time. This can result in a decrease in the disc space height. In addition, the facets and ligaments of the spine degenerate as well over time. These problems can lead to a reduction in the foramenal height of the vertebrae. The foramen is a natural opening between the vertebrae that allows the passage of respective nerves from the spinal cord. Because the nerves pass through the respective foramen, a reduction in the foramenal height may often causes nerve tissue to get pinched leading to various types of back pain. These pinched or compressed nerves can also lead to difficulty in walking.

Surgical solutions to this problem require the surgical removal of the ligaments and bone that are causing the compression. A number of interspinous process devices have been designed to act as spacers to flex the spine and open the canal, lateral recess and foramen to take pressure off of the compressed or pinched nerves. Designs vary from static spacers to dynamic, spring-like devices. These may be made from bone allograft, titanium, polyetheretherketone (PEEK), and elastomeric compounds. The common goal between these devices is to mechanically distract the spinous processes and blocking extension (of the abdominal muscles) that affect the intervertebral relationship. Examples of these include the X STOP device (Medtronic, Memphis, Tenn.), ExtenSure device (NuVasive, San Diego, Calif.), and the Wallis system (Abbott Spine, Bordeaux, France). Often, these devices are successful in alleviating symptoms of patients post surgery, however, many patients have recurring symptoms after months or years have passed.

SUMMARY OF THE INVENTION

The invention is an interspinous process device that is capable of providing distraction at multiple times after the initial surgery without requiring additional surgeries. In the first embodiment of the invention, an interspinous process device is configured for placement between adjacent spinous processes on a subject's spine. The device includes a housing configured for mounting to a first spinal process, the housing having a lead screw fixedly secured at one end thereof. A magnetic assembly is at least partially disposed within the housing and configured for mounting to a second spinal process. The magnetic assembly includes a hollow magnet configured for rotation within the magnetic assembly, the hollow magnet comprising a threaded insert configured to engage with the lead screw. An externally applied magnetic field rotates the hollow magnet in a first direction or a second, opposite direction. Rotation of the hollow magnet in the first direction causes telescopic movement of the magnetic assembly out of the housing (i.e., elongation) and rotation in the second direction causes telescopic movement of the magnetic assembly into the housing (i.e., shortening).

In a second aspect of the invention, a method of adjusting the distance between adjacent spinous processes in a subject includes affixing an interspinous process device to first and second spinous processes. The interspinous process device including a housing configured for mounting to the first spinal process, the housing comprising a lead screw fixedly secured at one end thereof. The interspinous device further includes a magnetic assembly at least partially disposed within the housing and configured for mounting to the second spinal process, the magnetic assembly comprising a hollow magnet configured for rotation within the magnetic assembly. The hollow magnet includes a threaded insert configured to engage with the lead screw. An external magnetic field is applied non-invasively to rotate the hollow magnet, wherein rotation of the hollow magnet in a first direction increases the distance between adjacent spinous processes and rotation of the hollow magnet in the second direction decreases the distance between adjacent spinous processes.

BRIEF DESCRIPTION OF THE DRAWINGS

FIG. 7A illustrates a cross-sectional representation of the external adjustment device being positioned on a patient's skin. FIG. 7A illustrates the hollow magnet in the 0° position.

FIG. 7B illustrates a cross-sectional representation of the external adjustment device being positioned on a patient's skin. FIG. 7B illustrates the hollow magnet in the 90° position.

FIG. 7C illustrates the hollow magnet in the 180° position.

FIG. 7D illustrates the hollow magnet in the 270° position.

DETAILED DESCRIPTION OF THE ILLUSTRATED EMBODIMENTS

Figure 1C:
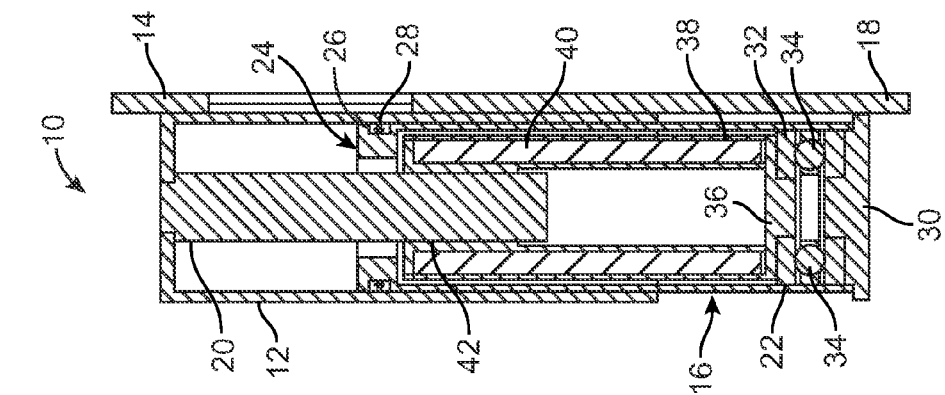
FIG. 1C illustrates a cross-sectional view of the interspinous process device of FIGS. 1A and 1B taken along the line C-C' of FIG. 1B.
Figure 1B:
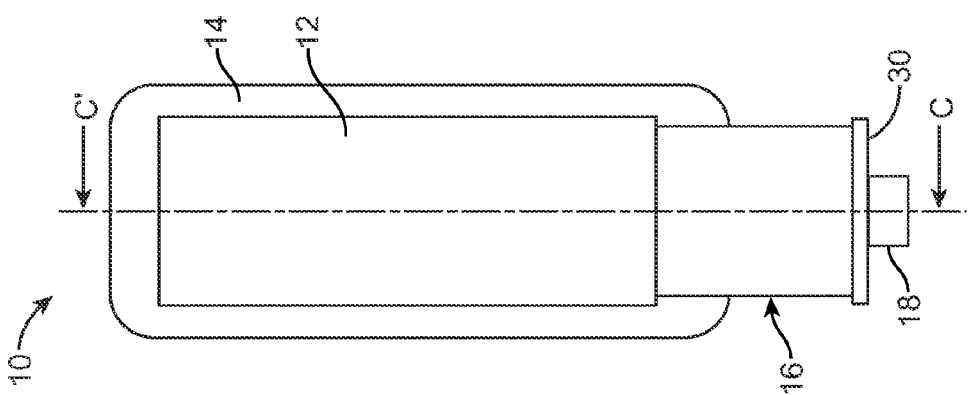
FIG. 1B illustrates a top plan view of the interspinous process device of FIG. 1A.
Figure 1A:
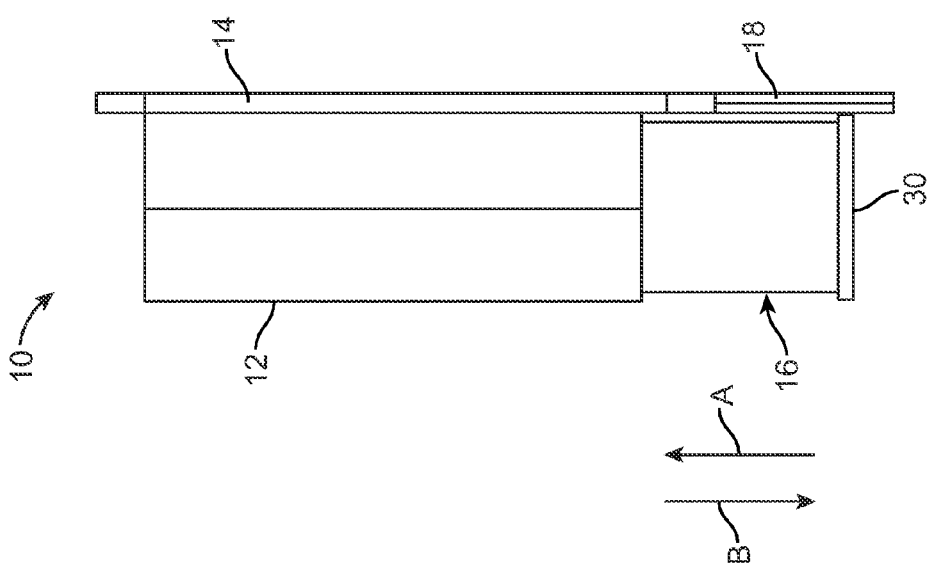
FIG. 1A illustrates side view of an interspinous process device according to one embodiment.
Figure 3:
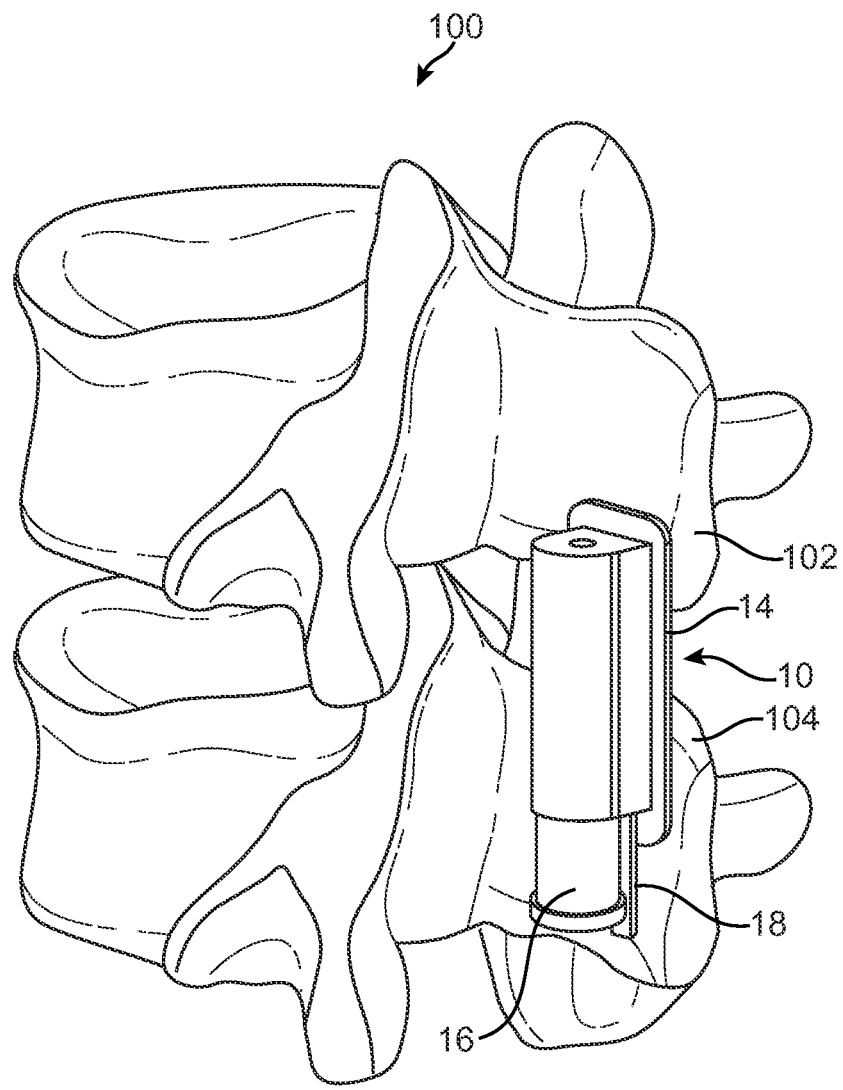
FIG. 3 illustrates an interspinous process device secured to adjacent spinous processes on a subject's spine.

FIGS. 1A, 1B, and 1B illustrate an interspinous process device 10 according to one embodiment. The interspinous process device 10 is configured to mount on a subject's spine 100 as illustrated in FIG. 3. For example, the interspinous process device 10 is mounted between adjacent spinous processes 102, 104. The interspinous process device 10 is configured to adjust its length in a non-invasive manner. As explained herein in more detail, an external adjustment device 1130 (FIGS. 4, 5, 6, 7A-7D, and 8) is provided that can lengthen or shorten the interspinous process device 10 on an as needed basis. The interspinous process device 10 includes a housing 12 that is affixed or otherwise coupled to a first mounting surface 14. The housing 12 may be made of any biocompatible, non-magnetic material such as, for instance, stainless steel, titanium or the like. A moveable magnetic assembly 16 is telescopically disposed within the housing 12. The magnetic assembly 16 is moveable in the direction of arrows A and B of FIG. 1A. The magnetic assembly 16 is affixed or otherwise coupled to a second mounting surface 18. The second mounting surface 18 is moveable with respect to the first mounting surface 14. In this regard, as the magnetic assembly 16 is advanced out of the housing 12, a distraction force is applied to the adjacent spinous processes 102, 104 (FIG. 3). This distraction force can be increased by advancing the device an additional amount. Conversely, as the magnetic assembly 16 is advanced into the housing 12, a compressive force (or relaxing as the case may be, for example, a decreased distraction force) is applied to the adjacent spinous processes 102, 104.

FIGS. 1A and 1B illustrate side and plan views, respectively, of the interspinous process device 10. FIG. 1C illustrates a cross-sectional view of the interspinous process device 10 taken along the line C-C' of FIG. 1B. As best seen in FIG. 1C, a lead screw 20 is fixedly secured at one end to the housing 12. The lead screw 20 has threads having, preferably, a very fine pitch, for example, 80 to 100 threads per inch, in order to minimize friction between the lead screw 20 and the a threaded insert (described in more detail below), and thus, minimize the required torque. The materials of the lead screw 20 may be made from non-magnetic, implantable materials such as titanium, though they may also be made from other magnetic materials such as stainless steel. Additionally, lubrication may be added to the lead screw and/or threaded insert to further minimize friction. For example, biocompatible silicone or Krytox® (perfluorinated polyether-based oil available from DuPont) may be added.

Turning now to the magnetic assembly 16, which is best illustrated in FIG. 1C, the magnetic assembly 16 itself includes a housing 22 that terminates at one end at an o-ring gland 24. The o-ring gland 24 includes a recess 26 dimensioned to receive an o-ring 28 that is compressed between an inner surface of the housing 12 and the recess 26. The o-ring 28 thus provides a dynamic sealing surface as the magnetic assembly 16 moves into and out of the housing 12. The opposing end of the magnetic assembly 16 includes an end cap 30 that effectively seals the interior of the magnetic assembly 16 from the external environment. End cap 30 is joined with housing 12 by various methods, for example laser or E-beam welding. Adjacent to the end cap 30 is a thrust bearing 32 that includes a plurality of ball bearings 34 and a central aperture (not shown) dimensioned to receive an axle 36 of a retaining cup 38. The retaining cup 38 is thus rotationally mounted with respect to the thrust bearing 32. The retaining cup 38 may be made of stainless steel or a non-magnetic material such as titanium.

Still referring to FIG. 1C, a hollow magnet 40 is mounted inside the retaining cup 38. The hollow magnet 40 may include, for example, a permanent magnet. The hollow magnet 40 may be formed from a rare earth magnet, preferably Neodynium-Iron-Boron. Other magnetic materials may be used, including SmCo (Samarium Cobalt), which is typically available as $SmCo_5$, or $SmCo_{15}$, $Sm_2Co_{17}$, or AlNiCo (Aluminum Nickel Cobalt). In still other embodiments, Iron Platinum (Fe—Pt) may be used. The hollow magnet 40 may be bonded to the interior of the retaining cup 38 using, for example, an adhesive or epoxy. A threaded insert 42 having a female thread is located in the hollow portion of the magnet 40. FIG. 1C illustrates the threaded insert 42 that is located at one end of the hollow magnet 40. The threaded insert 42 is bonded or otherwise affixed to an inner surface of the hollow magnet 40 so that when the hollow magnet 40 rotates, the threaded insert 42 rotates in unison.

Figure 2:
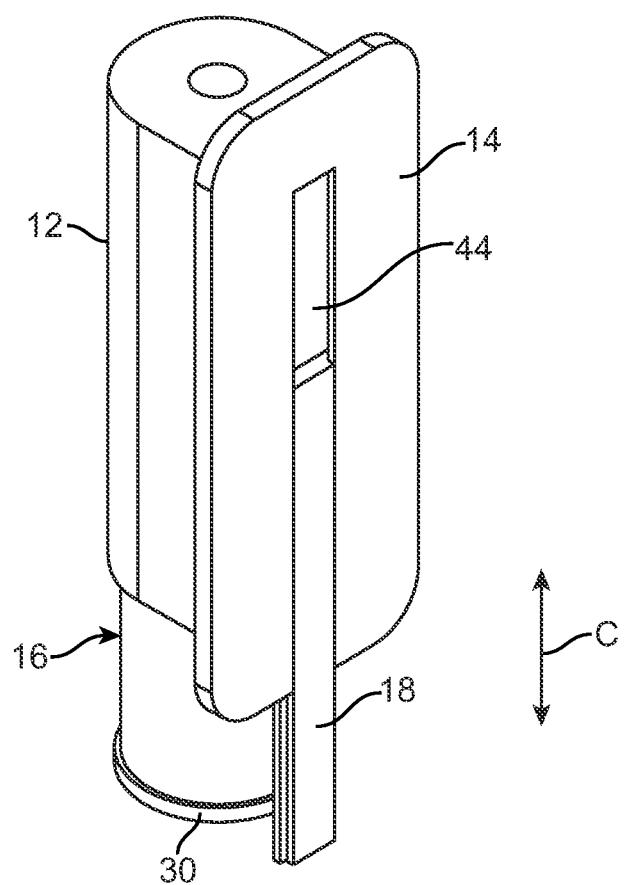
FIG. 2 illustrates a perspective view of the interspinous process device.

As explained in more detail below, an external magnetic field is applied to the subject having the implanted interspinous process device 10. The interspinous process device 10 can then be lengthened or shortened to increase or decrease the foramenal height of the vertebrae. FIG. 2 illustrates a perspective view of the interspinous process device 10 with the first and second mounting surfaces 14, 18 exposed for better viewing. As seen in FIG. 2, a channel 44 is provided in the first mounting surface 14 and is dimensioned to receive the second mounting surface 18. The channel 44 may be milled or otherwise formed with a step or other geometry that enables the second mounting surface 18 to slide back and forth in the direction of arrow C. A low friction coating may be applied to the channel 44 and/or the interface with the second mounting surface 18 to reduce frictional forces. The first and second mounting surfaces 14, 18 may be affixed to the adjacent spinous processes 102, 104 using any number of affixation techniques known to those skilled in the art. These include, for example, screws, hooks, clamps, and the like. FIG. 3 illustrates an interspinous process device 10 mounted between adjacent spinous processes 102, 104. In this view, the actual affixation mechanism is omitted to better illustrate the relationship between the interspinous process device 10 and the spinous processes 102, 104.

Figure 9:
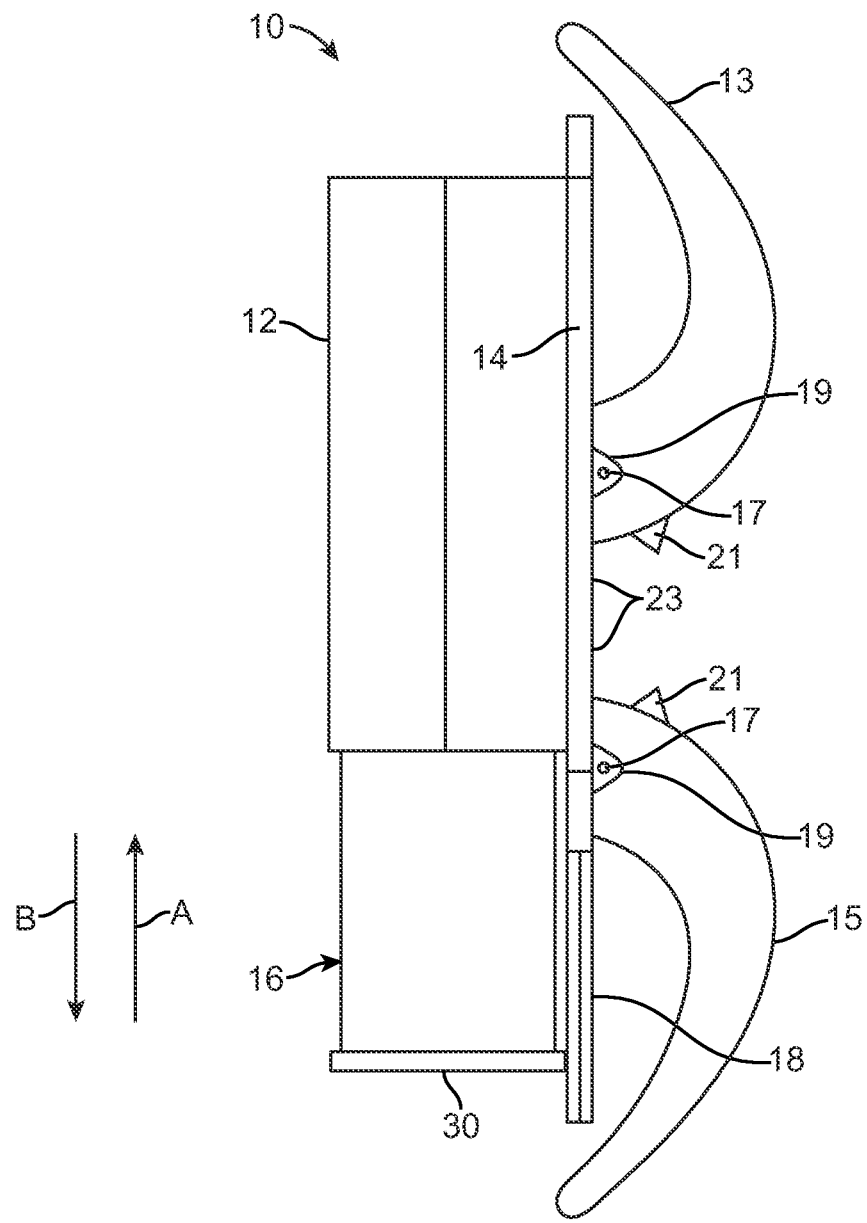
FIG. 9 illustrates side view of an interspinous process device according to another embodiment. Hooks are illustrated in a low-profile configuration.
Figure 10:
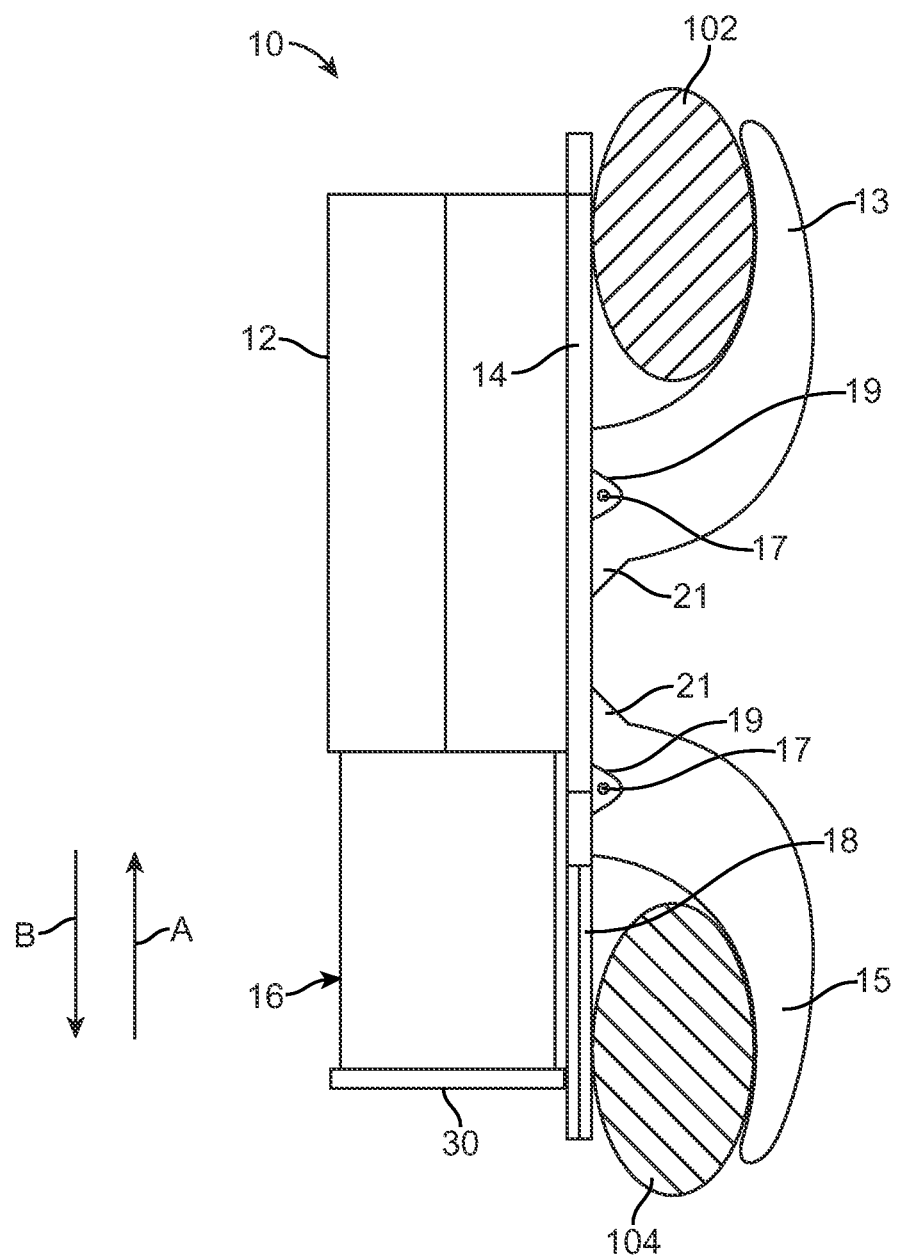
FIG. 10 illustrates side view of an interspinous process device according to another embodiment. Hooks are illustrated in a deployed configuration.

FIGS. 9 and 10 show an embodiment having two upward facing hooks 13 (one hook obscured from view) coupled to the two sides of the first mounting surface 14 and one downward facing hook 15 coupled to the second mounting surface 18. Upward facing hooks 13 are configured for cradling the lower portion of spinous process 102, and downward facing hook 15 is configured for cradling the upper portion of spinous process 104, allowing the positive displacement of the interspinous process device 10 to distract between the spinous processes 102, 104. Hooks 13, 15 may additionally be configured to be able to fold, retract, or pivot out of the way during insertion to allow for a less invasive insertion (e.g., a smaller incision results in less trauma). Hooks 13, 15 are attached to interspinous process device 10 with axles 17 extending between pairs of mounts 19. The axles 17 extend through holes (not shown) in hooks 13, 15. FIG. 9 shows the embodiment with the hooks 13, 15 folded or pivoted out of the way for a lower profile, and FIG. 10 shows the hooks 13, 15 in position to distract spinous processes 102, 104. Stops 21 are configured to abut flat surface 23 so that hooks 13, 15 are held static in the configuration of FIG. 10.

Figure 4:
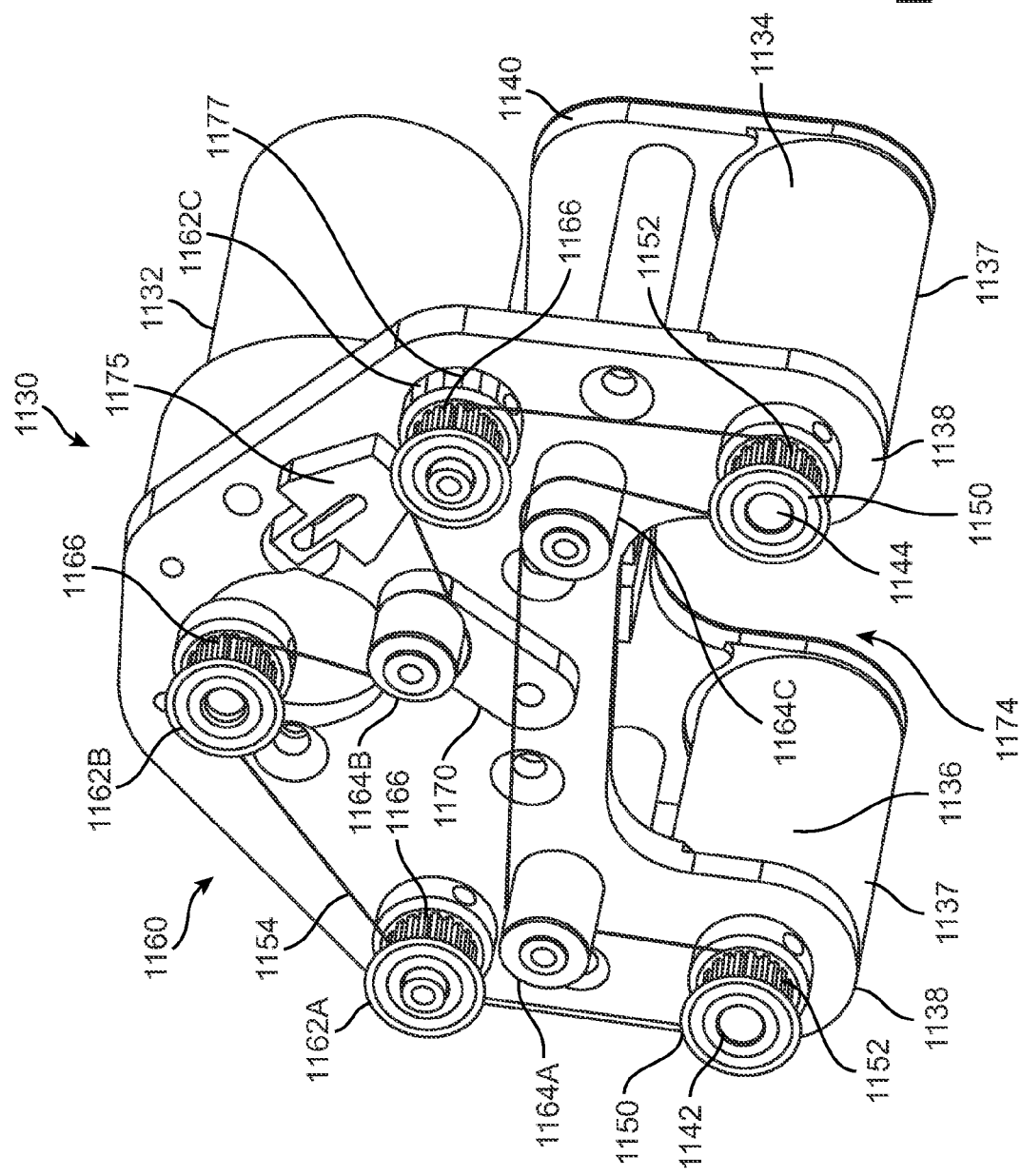
FIG. 4 illustrates a perspective view of an external adjustment device according to one embodiment. The outer housing or cover is removed to illustrate the various aspects of the external adjustment device.

FIG. 4 illustrates an external adjustment device 1130 that may be used to externally impart rotational motion or "drive" the magnetic assembly 16. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 4, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the longitudinal axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the magnetic assembly 16 (not shown in FIGS. 7A-7D for clarity purposes).

As seen in FIG. 4, the permanent magnets 1134, 1136 are rotationally mounted between opposing base members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 4, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 5) contained within a drive belt (indicated by path 1154) or drive chain.

Figure 6:
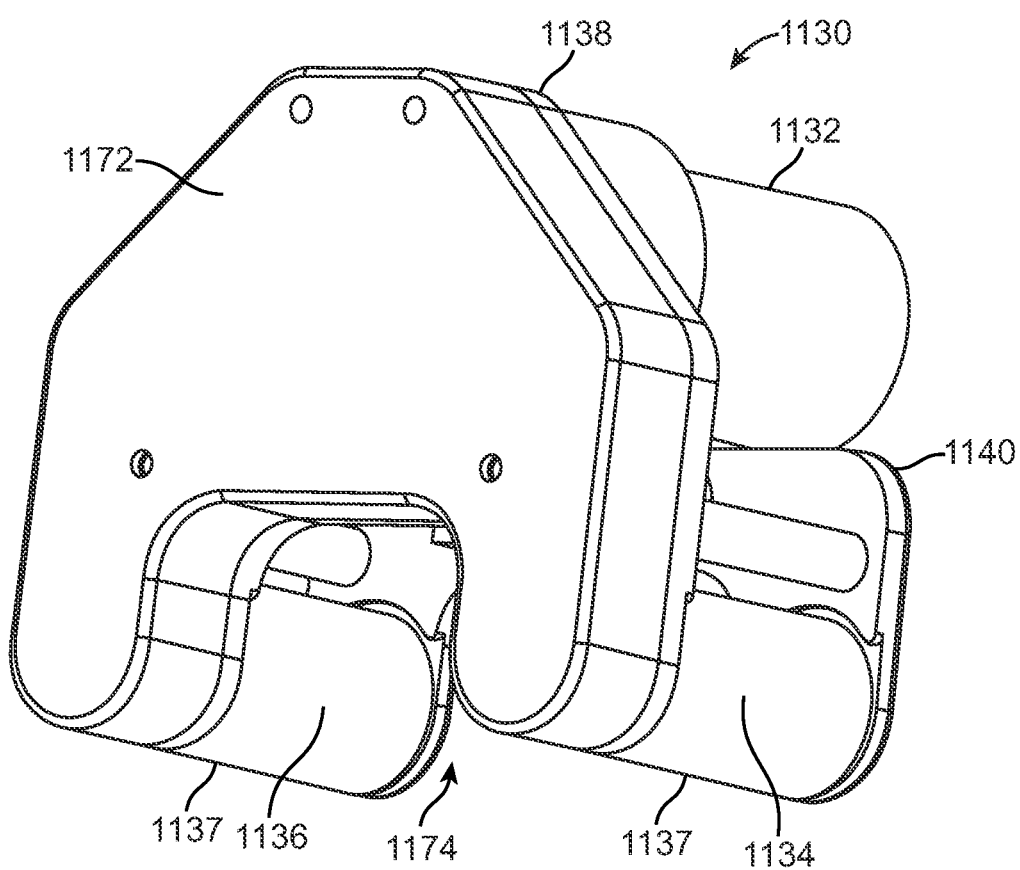
FIG. 6 illustrates a perspective view of an external adjustment device of FIG. 4 with the outer housing or cover in place.

Still referring to FIG. 4, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154 or drive chain. Pulleys 1162A, 1162B, 1162C and rollers 1164A, 1164B, 1164C may be mounted on respective bearings (not shown). As seen in FIG. 4, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 6). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it. The external adjustment device 1130 may also be supplied in a case, for example, a case that has a sheet made of a magnetic shielding material, to minimize the magnetic field external to the case. Giron or mu-metal are two examples of this material.

Figure 5:
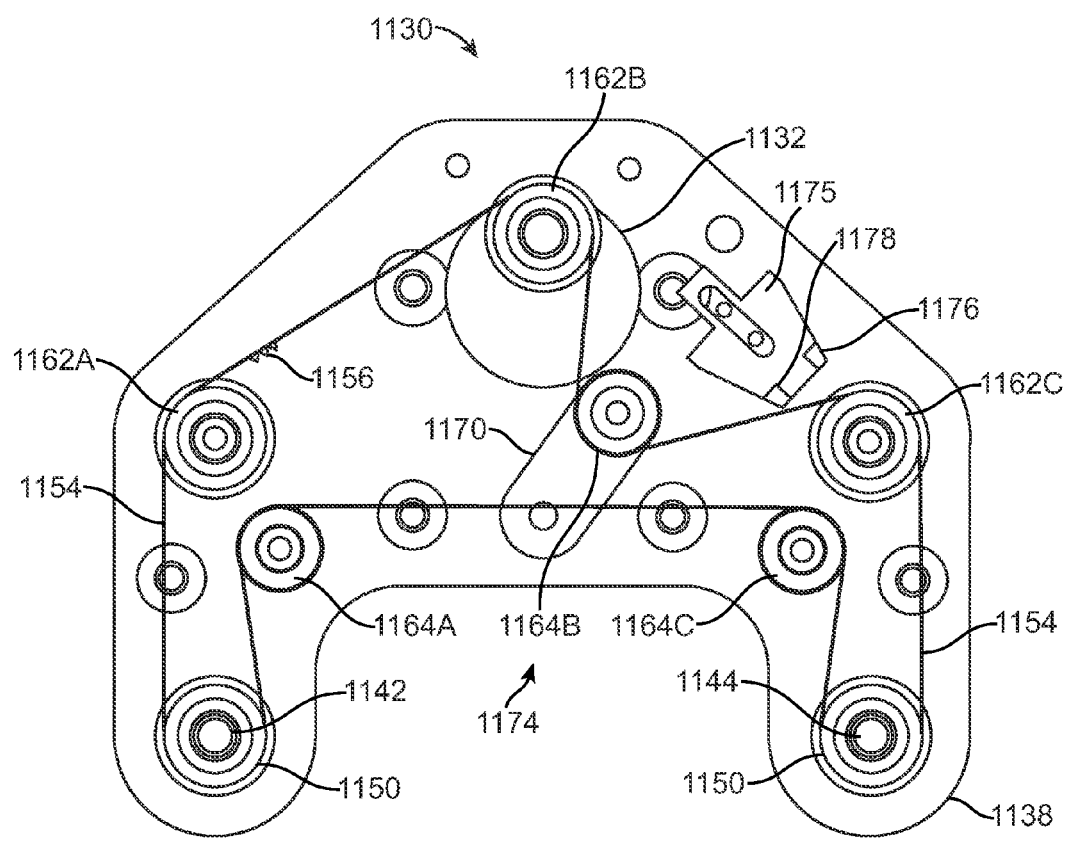
FIG. 5 illustrates a side or end view of the external adjustment device of FIG. 4.

As seen in FIGS. 4 and 5, rotational movement of the pulley 1162B causes the drive belt 1154 to move around the various pulleys 1150, 1162A, 1162B, 1162C and rollers 1164A, 1164B, 1164C. In this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). A small permanent magnet may be temporarily placed on the patient's clothing to determine the location of the hollow magnet 40 (via the attraction of the two magnets). The recess 1174 allows skin as well as the underlying tissue to gather or compress within the recessed region 1174 as seen in FIGS. 7A and 7B. This advantageously reduces the overall distance between the external drive magnets 1134, 1136 and the hollow magnet 40 contained within the magnetic assembly 16. By reducing the distance, this means that the externally located magnets 1134, 1136 and/or the hollow magnet 40 may be made smaller. This reduction in distance is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

Figure 7C:
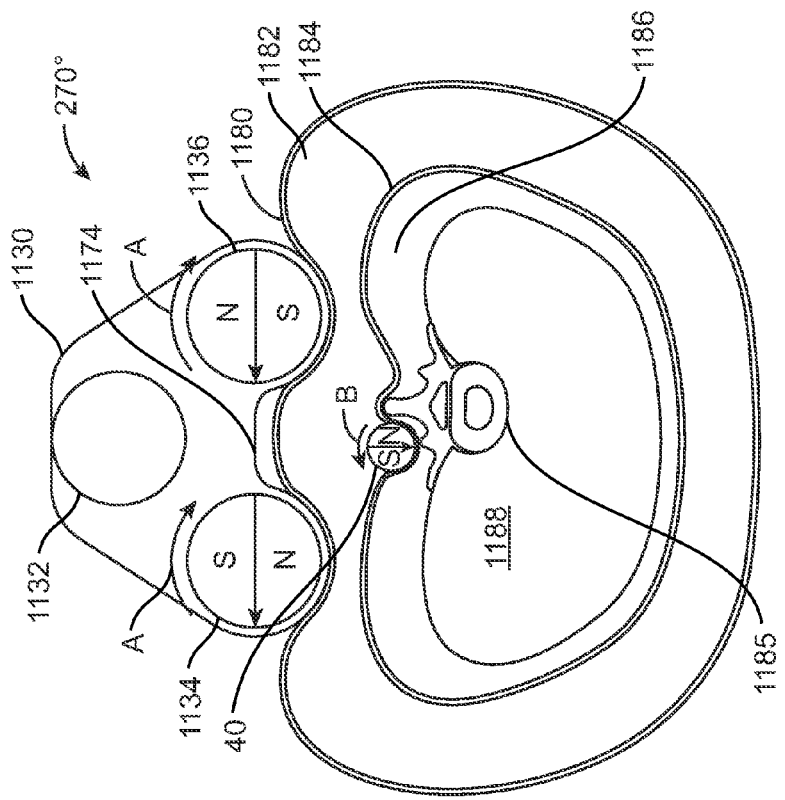
FIG. 7C illustrates a cross-sectional representation of the external adjustment device being positioned on a patient's skin.

FIGS. 7A and 7B illustrate cross-sectional views of the patient having an implanted magnetic assembly (not shown for sake of clarity) with a hollow magnet 40. The hollow magnet 40 is seen disposed on one side of a vertebra 1185 although the hollow magnet 40 may be located elsewhere depending on the particular affixation point on the spinous processes. FIGS. 7A and 7B illustrate an obese patient in which skin and other tissue gather within the recess 1174. As seen in FIGS. 7A and 7B the excess skin and other tissue are easily accommodated within the recess 1174 to enable close positioning between the hollow magnet 40 and the external drive magnets 1134, 1136. For many patients, the air gap or distance between the hollow magnet 40 and the external drive magnets 1134, 1136 is generally one inch or less. In FIGS. 7A through 7D, the hollow magnet 40 is depicted somewhat larger than its actual size in order for its respective poles to be more clearly visible.

Still referring to FIGS. 4 and 5, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may includes a LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 7A, 7B, 7C, and 7D illustrate the progression of the external magnets 1134, 1136 and the hollow magnet 40 that is located within the magnetic assembly 16 during use. FIGS. 7A, 7B, 7C, and 7D illustrate the external adjustment device 1130 being disposed against the external surface of the patient's skin 1180 adjacent the spine. In the non-invasive adjustment procedure depicted, the patient 100 lies in a prone position, and the external adjustment device 1130 is placed upon the patient's back. However, the adjustment is conceived possible with the patient in supine, standing or other positions. The external adjustment device 1130 is placed against the skin 1180 in this manner to remotely rotate the hollow magnet 40. As explained herein, rotation of the hollow magnet 40 causes rotational movement of the threaded insert 42. This rotational movement is then translated to the lead screw 20. Depending on the rotational direction of the lead screw 20, the magnetic assembly 16 moves in a telescopic manner out of or into the housing 12. In this regard, by controlling the rotational movement of the hollow magnet 40 using the external adjustment device 1130, the operator is able to adjust the linear displacement of the interspinous process device 10 in a controllable manner. The hollow magnet 40 may have rotational movement though less than 360° of a full rotation. Alternatively, the hollow magnet 40 may have rotational movement through more than 360° (e.g., multiple, full revolutions).

As seen in FIGS. 7A, 7B, 7C, and 7D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 7A, 7B, 7C, and 7D show the magnetic orientation of the hollow magnet 40 as it undergoes a full rotation in response to movement of the permanent magnets 1134, 1136 of the external adjustment device 1130.

With reference to FIG. 7A, the hollow magnet 40 is shown being oriented with respect to the two permanent magnets 1134, 1136 via an angle θ. This angle θ may depend on a number of factors including, for instance, the separation distance between the two permanent magnets 1134, 1136, the location or depth of where the hollow magnet 40 is located, the degree of force at which the external adjustment device 1130 is pushed against the patient's skin. Generally in applications including some obese patients, the angle θ should be at or around 90° to achieve maximum drivability (e.g., torque). An angle of about 70° is preferred for the majority of patients when the permanent magnets 1134, 1136 have an outer diameter of about two (2.0) to three (3.0) inches.

FIG. 7A illustrates the initial position of the two permanent magnets 1134, 1136 and the hollow magnet 40. This represents the initial or starting location (e.g., 0° position as indicated). Of course, it should be understood that, during actual use, the particular orientation of the two permanent magnets 1134, 1136 and the hollow magnet 40 will vary and not likely will have the starting orientation as illustrated in FIG. 7A. In the starting location illustrated in FIG. 7A, the two permanent magnets 1134, 1136 are oriented with their poles in an N-S/S-N arrangement. The hollow magnet 40 is, however, oriented generally perpendicular to the poles of the two permanent magnets 1134, 1136.

Figure 7D:
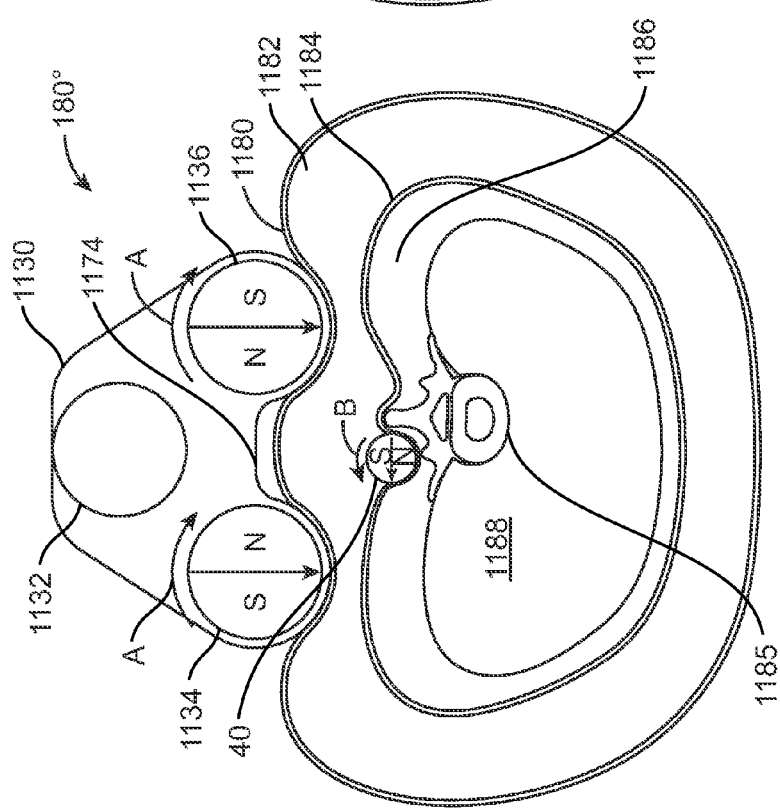
FIG. 7D illustrates a cross-sectional representation of the external adjustment device being positioned on a patient's skin.

FIG. 7B illustrates the orientation of the two permanent magnets 1134, 1136 and the hollow magnet 40 after the two permanent magnets 1134, 1136 have rotated through 90°. The two permanent magnets 1134, 1136 rotate in the direction of arrow A (e.g., clockwise) while the hollow magnet 40 rotates in the opposite direction (e.g., counter clockwise) represented by arrow B. It should be understood that the two permanent magnets 1134, 1136 may rotate in the counter clockwise direction while the hollow magnet 40 may rotate in the clockwise direction. Rotation of the two permanent magnets 1134, 1136 and the hollow magnet 40 continues as represented by the 180° and 270° orientations as illustrated in FIGS. 7C and 7D. Rotation continues until the starting position) (0°) is reached again.

During operation of the external adjustment device 1130, the permanent magnets 1134, 1136 may be driven to rotate the hollow magnet 40 through one or more full rotations in either direction to increase or decrease the foramenal distance between spinous processes 102, 104. Of course, the permanent magnets 1134, 1136 may be driven to rotate the hollow magnet 40 through a partial rotation as well (e.g., ¼, ⅛, 1/16, etc.). The use of two magnets 1134, 1136 is preferred over a single external magnet because the hollow magnet 40 may not be oriented perfectly at the start of rotation, so one external magnet 1134, 1136 may not be able to deliver its maximum torque, which depends on the orientation of the hollow magnet 40 some degree. However, when two (2) external magnets (1134, 1136) are used, one of the two 1134 or 1136 will have an orientation relative to the hollow magnet 40 that is better or more optimal than the other. In addition, the torques imparted by each external magnet 1134, 1136 are additive. In prior art magnetically driven devices for other medical applications, the external driving device is at the mercy of the particular orientation of the internal driven magnet. The two-magnet embodiment described herein is able to guarantee a larger driving torque—as much as 75% more than a one-magnet embodiment in the spinal application—and thus the hollow magnet 40 can be designed smaller in dimension, and less massive. A smaller hollow magnet 40 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

Figure 8:
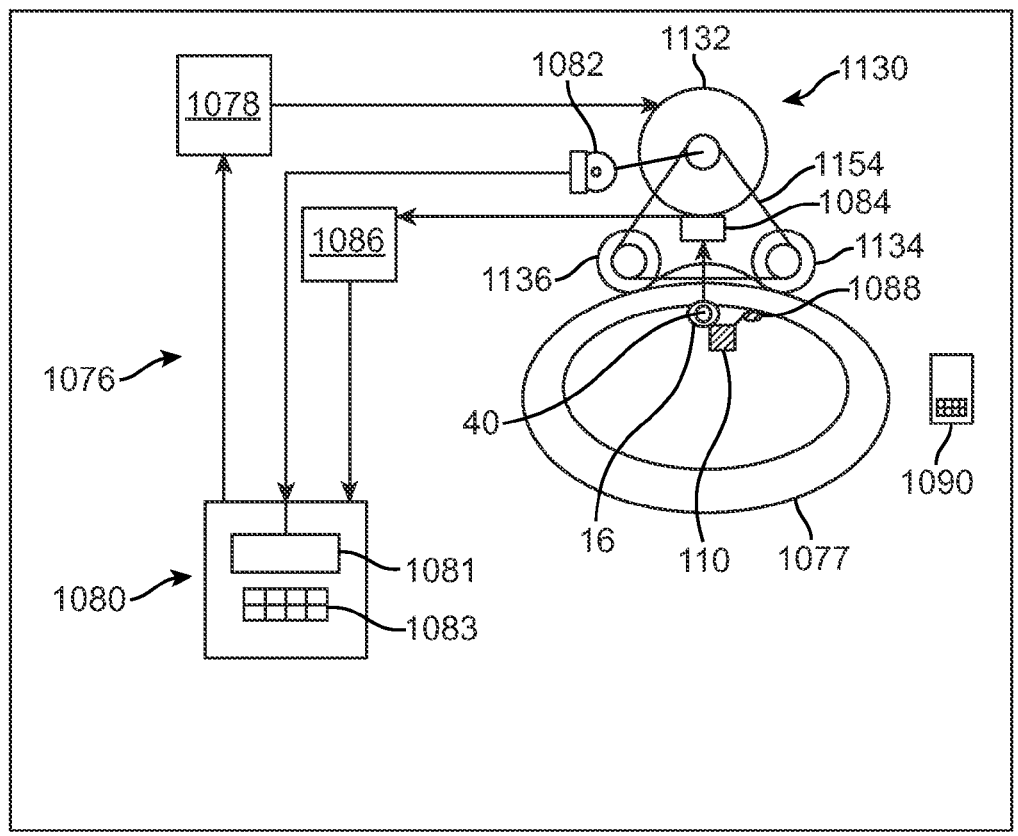
FIG. 8 schematically illustrates a system for driving the external adjustment device according to one embodiment.

FIG. 8 illustrates a system 1076 according to one aspect of the invention for driving the external adjustment device 1130. FIG. 8 illustrates the external adjustment device 1130 pressed against the surface of a patient 1077 (torso face down shown in cross-section). The portion of the magnetic assembly 16 containing the hollow magnet 40 is illustrated. The hollow magnet 40 that is located within the magnetic assembly 16 (disposed internally within the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the hollow magnet 40. Turning hollow magnet 40 in one direction causes the interspinous process device 10 to lengthen, or increase distraction force while turning in the opposite direction causes the interspinous process device 10 to shorten, or decrease distraction force. Changes to the interspinous process device 10 are directly related to the number of turns of the hollow magnet 40. In an alternative embodiment, a ratchet may be added which allows motion in one direction, but not the other. For example, the device could be made to be extendable, but not retractable.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 4-5. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the hollow magnet 40. The sensor 1084 may acquire positional information using, for example, sound waves, ultrasonic waves, radiation (e.g., light), or even changes or perturbations in the magnetic or electromagnetic field between the hollow magnet 40 and the external magnets 1134, 1136. For example, the sensor 1084 may detect photons or light that is reflected from the hollow magnet 40 or a coupled structure (e.g., rotor) that is attached thereto. For example, light may be passed through the patient's skin and other tissue at wavelength(s) conducive for passage through tissue. Portions of the hollow magnet 40 or associated structure may include a reflective surface that reflects light back outside the patient as the hollow magnet 40 (for instance the magnetic assembly 16 may transmit light at least partially there through). The reflected light can then be detected by the sensor 1084 which may include, for example, a photodetector or the like.

In another aspect, the sensor 1084 may operate on the Hall effect, wherein two additional magnets are located within the interspinous process device 10. The additional magnets move axially in relation to each other as the hollow magnet 40 rotates and therefore as the distraction increases or decreases, allowing the determination of the current size of the interspinous process device 10. In yet another aspect, the sensor 1084 may be a strain gauge, capable of determining the distraction force. A strain gauge or force transducer disposed on a portion of the interspinous process device 10 may also be used as an implantable feedback device. For example, the strain gauge may be able to communicate wirelessly the actual distraction force applied to the spine by the interspinous process device 10. A wireless reader or the like (that also can inductively power the strain gauge) may be used to read the distraction forces. One exemplary strain gauge sensor is the EMBEDSENSE wireless sensor, available from MicroStrain, Inc. of Williston, Vt. 05495. The EMBEDSENSE wireless sensor uses an inductive link to receive power form an external coil and returns digital stain measurements wirelessly.

In the embodiment of FIG. 8, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the hollow magnet 40. For example, the hollow magnet 40 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). Alternatively, rotation of the hollow magnet 40 in one direction (e.g., clockwise) may produce a relatively loud click while rotation in the opposite direction may produce a relatively quiet click. The amplified and filtered signal from the signal processing circuit 1086 can then pass to the PLC 1080. As an alternative to using a microphone sensor 1084 and associated circuitry, medical personnel may listen for the clicks using a stethoscope or similar instrument.

Additional details regarding the operation of various acoustic and other detection modalities may be found in U.S. patent application Ser. No. 12/121,355, published as U.S. Patent Application Publication No. 2009-0112262, which is incorporated herein by reference.

During operation of the system 1076, each patient will have a number or indicia that correspond to the adjustment setting or size of their interspinous process device 10. This number can be stored on an optional storage device 1088 (as shown in FIG. 8) that is carried by the patient (e.g., memory card, magnetic card, or the like) or is integrally formed with the interspinous process device 10. For example, a RFID tag 1088 implanted either as part of the system or separately may be disposed inside the patient (e.g., subcutaneously or as part of the device) and can be read and written via an antenna 1090 to update the current size of the interspinous process device 10. In one aspect, the PLC 1080 has the ability to read the current number corresponding to the size or setting of the interspinous process device 10 from the storage device 1088. The PLC 1080 may also be able to write the adjusted or more updated current size or setting of the interspinous process device 10 to the storage device 1088. Of course, the current size may recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag

1088 may be used as a security device. For example, the RFID tag 1088 may be used to allow only physicians to adjust the interspinous process device 10 and not patients. Alternatively, the RFID tag 1088 may be used to allow only certain models or makes of interspinous process devices to be adjusted by a specific model or serial number of external adjustment device 1130.

In one aspect, the current size or setting of the interspinous process device 10 is input into the PLC 1080. This may be done automatically or through manual input via, for instance, the keyboard 1083 that is associated with the PLC 1080. The PLC 1080 thus knows the patient's starting point. If the patient's records are lost, the length of the interspinous process device 10 may be measured by X-ray and the PLC 1080 may be manually programmed to this known starting point.

The external adjustment device 1130 is commanded to make an adjustment. This may be accomplished via a pre-set command entered into the PLC 1080 (e.g. "increase distraction displacement of interspinous process device 10 by 0.5 mm" or "increase distraction force of interspinous process device 10 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 8, or through another shaft or surface that is mechanically coupled to the motor 1132. For example, the encoder 1082 may read the position of markings 1177 located on the exterior of a pulley 1162C like that disclosed in FIG. 4. Every rotation or partial rotation of the motor 1132 can then be counted and used to calculate the adjusted or new size or setting of the interspinous process device 10.

The sensor 1084, which may include a microphone sensor 1084, may be monitored continuously. For example, every rotation of the motor 1132 should generate the appropriate number and pitch of clicks generated by rotation of the hollow magnet 40 inside the interspinous process device 10. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch but the external adjustment device 1130 was configured to lengthen).

While embodiments of the present invention have been shown and described, various modifications may be made without departing from the scope of the present invention. For example, the device can be used for treatment of various descriptions of the source of back pain: spondylolisthesis, degenerative spinal stenosis, disc herniations, instability, discogenic back pain, facet syndrome, and thecal sac changes to name a few. The invention, therefore, should not be limited, except to the following claims, and their equivalents.

What is claimed is:

1. An interspinous process device configured for placement between adjacent spinous processes on a subject's spine comprising:
    a housing configured for mounting to a first spinous process, the housing comprising a lead screw fixedly secured at one end thereof and a first mounting surface, wherein the first mounting surface comprises a channel in a surface of the first mounting surface;
    a magnetic assembly at least partially disposed within the housing and configured for mounting to a second spinous process, the magnetic assembly comprising a hollow magnet having a longitudinally extending bore defining an inner surface, the bore extending in a direction substantially between the first spinous process and the second spinous process, the hollow magnet configured for rotation within the magnetic assembly, the hollow magnet comprising an internally threaded insert affixed to the inner surface of the bore, the internally threaded insert configured to coaxially engage with the lead screw;
    a second mounting surface coupled to the magnetic assembly, wherein the second mounting surface is dimensioned to fit into and slide within the channel; and
    wherein an externally applied magnetic field rotates the hollow magnet, wherein rotation of the hollow magnet in a first direction effectuates telescopic movement of the magnetic assembly out of the housing.

2. The interspinous process device of claim 1, wherein rotation of the hollow magnet in a second, opposite direction causes telescopic movement of the magnetic assembly into the housing.

3. The interspinous process device of claim 1, further comprising a seal disposed between the magnetic assembly and an internal surface of the housing.

4. The interspinous process device of claim 1, the magnetic assembly comprising a retaining cup configured to rotatably support the hollow magnet within the magnetic assembly.

5. The interspinous process device of claim 4, further comprising a thrust bearing, wherein an end of the retaining cup is rotationally supported by the thrust bearing.

6. The interspinous process device of claim 1, wherein one or both of the housing and magnetic assembly further comprise a screw configured to secure to respective spinous processes.

7. The interspinous process device of claim 1, wherein one or both of the housing and magnetic assembly further comprise a hook configured to secure to respective spinous processes.

8. The interspinous process device of claim 1, further comprising at least one hook configured to pivot between a low profile configuration and a deployed configuration.

9. The interspinous process device of claim 1, wherein one or both of the housing and magnetic assembly further comprise a clip configured to secure to respective spinous processes.

10. The interspinous process device of claim 1, further comprising an external adjustment device configured to apply an external, noninvasively applied magnetic field to the hollow magnet.

11. The interspinous process device of claim 10, the external adjustment device comprising a feedback sensor configured to determine positional data of the magnetic assembly.

12. The interspinous process device of claim 11, wherein the feedback sensor detects one or more of an acoustic signal, a radiation signal, or a magnetic signal.

13. The interspinous process device of claim 1, further comprising at least one force feedback sensor.

14. A method of adjusting the distance between adjacent spinous processes in a subject comprising:
    affixing an interspinous process device to first and second spinous processes, the interspinous process device comprising a housing configured for mounting to the first spinous process, the housing comprising a lead screw fixedly secured at one end thereof and a first mounting surface, wherein the first mounting surface comprises a channel in a surface of the first mounting surface, the interspinous device further comprising a magnetic assembly at least partially disposed within the housing and configured for mounting to the second spinous process, the magnetic assembly comprising a hollow magnet having a longitudinally extending bore defining an inner surface and a second mounting surface coupled to the magnetic assembly, the bore extending in a direction substantially between the first spinous process and the second spinous process, the hollow magnet configured for rotation within the magnetic assembly, the hollow magnet comprising an internally threaded insert affixed to the inner surface of the bore, the internally threaded insert configured to coaxially engage with the lead screw, and the second mounting surface dimensioned to fit into and slide within the channel; and applying a non-invasive external magnetic field to rotate the hollow magnet, wherein rotation of the hollow magnet in a first direction increases the distance between adjacent spinous processes.

15. The method of claim 14, wherein rotation of the hollow magnet in a second direction decreases the distance between adjacent spinous processes.

16. The method of claim 14, wherein the external magnetic field is applied from an external adjustment device comprising one or more permanent magnets.

17. The method of claim 16, wherein the external adjustment device is placed against the skin or clothing of the subject.

18. The method of claim 16, wherein the external magnetic field is applied to the subject periodically.

19. An interspinous process device configured for placement between adjacent spinous processes on a subject's spine comprising:
 a housing configured for mounting to a first spinous process, the housing comprising a lead screw fixedly secured to an inner surface of the housing at one end thereof;
 a magnetic assembly at least partially disposed within the housing and configured for mounting to a second spinous process, the magnetic assembly comprising a hollow magnet having a longitudinally extending bore defining an inner surface, the bore extending in a direction substantially between the first spinous process and the second spinous process, the hollow magnet configured for rotation within the magnetic assembly, the hollow magnet comprising an internally threaded insert affixed to the inner surface of the bore, the internally threaded insert configured to coaxially engage with the lead screw; and
 wherein an externally applied magnetic field rotates the hollow magnet, wherein rotation of the hollow magnet in a first direction effectuates telescopic movement of the magnetic assembly out of the housing.

20. The interspinous process device of claim 19, wherein rotation of the hollow magnet in a second, opposite direction causes telescopic movement of the magnetic assembly into the housing.

21. The interspinous process device of claim 19, further comprising a seal disposed between the magnetic assembly and an internal surface of the housing.

22. The interspinous process device of claim 19, the magnetic assembly comprising a retaining cup configured to rotatably support the hollow magnet within the magnetic assembly.

23. The interspinous process device of claim 22, further comprising a thrust bearing, wherein an end of the retaining cup is rotationally supported by the thrust bearing.

24. The interspinous process device of claim 19, wherein one or both of the housing and magnetic assembly further comprise a screw configured to secure to respective spinous processes.

25. The interspinous process device of claim 19, wherein one or both of the housing and magnetic assembly further comprise a hook configured to secure to respective spinous processes.

26. The interspinous process device of claim 19, further comprising at least one hook configured to pivot between a low profile configuration and a deployed configuration.

27. The interspinous process device of claim 19, wherein one or both of the housing and magnetic assembly further comprise a clip configured to secure to respective spinous processes.

28. The interspinous process device of claim 19, further comprising an external adjustment device configured to apply an external, noninvasively applied magnetic field to the hollow magnet.

29. The interspinous process device of claim 28, the external adjustment device comprising a feedback sensor configured to determine positional data of the magnetic assembly.

30. The interspinous process device of claim 29, wherein the feedback sensor detects one or more of an acoustic signal, a radiation signal, or a magnetic signal.

31. The interspinous process device of claim 19, further comprising at least one force feedback sensor.

32. A method of adjusting the distance between adjacent spinous processes in a subject comprising:
 affixing an interspinous process device to first and second spinous processes, the interspinous process device comprising a housing configured for mounting to the first spinous process, the housing comprising a lead screw fixedly secured to an inner surface of the housing at one end thereof, the interspinous device further comprising a magnetic assembly at least partially disposed within the housing and configured for mounting to the second spinous process, the magnetic assembly comprising a hollow magnet having a longitudinally extending bore defining an inner surface, the bore extending in a direction substantially between the first spinous process and the second spinous process, the hollow magnet configured for rotation within the magnetic assembly, the hollow magnet comprising an internally threaded insert affixed to the inner surface of the bore, the internally threaded insert configured to coaxially engage with the lead screw; and
 applying a non-invasive external magnetic field to rotate the hollow magnet, wherein rotation of the hollow magnet in a first direction increases the distance between adjacent spinous processes.

33. The method of claim 32, wherein rotation of the hollow magnet in a second direction decreases the distance between adjacent spinous processes.

34. The method of claim 32, wherein the external magnetic field is applied from an external adjustment device comprising one or more permanent magnets.

35. The method of claim 34, wherein the external adjustment device is placed against the skin or clothing of the subject.

36. The method of claim 34, wherein the external magnetic field is applied to the subject periodically.

\* \* \* \* \*